(12) United States Patent
Kaza et al.

(10) Patent No.: US 9,301,814 B2
(45) Date of Patent: *Apr. 5, 2016

(54) SYSTEM AND METHOD FOR DIGITAL TOOTH IMAGING

(71) Applicant: Align Technology, Inc., San Jose, CA (US)

(72) Inventors: Srinivas Kaza, San Francisco, CA (US); Bob Grove, San Jose, CA (US)

(73) Assignee: Align Technology, Inc., San Jose, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/670,137

(22) Filed: Mar. 26, 2015

(65) Prior Publication Data

US 2015/0202025 A1 Jul. 23, 2015

Related U.S. Application Data

(60) Continuation of application No. 13/051,759, filed on Mar. 18, 2011, now Pat. No. 8,995,732, which is a division of application No. 11/678,749, filed on Feb. 26, 2007, now Pat. No. 7,916,911.

(51) Int. Cl.

| | |
|---|---|
| G06K 9/00 | (2006.01) |
| G06K 9/36 | (2006.01) |
| G06K 9/32 | (2006.01) |
| A61C 3/00 | (2006.01) |
| A61C 11/00 | (2006.01) |
| A61C 9/00 | (2006.01) |
| A61C 7/00 | (2006.01) |
| A61C 7/08 | (2006.01) |
| G06F 19/12 | (2011.01) |

(52) U.S. Cl.
CPC . *A61C 7/002* (2013.01); *A61C 7/08* (2013.01); *A61C 9/00* (2013.01); *A61C 9/0046* (2013.01); *A61C 9/0053* (2013.01); *G06F 19/12* (2013.01)

(58) Field of Classification Search
None
See application file for complete search history.

(56) References Cited

U.S. PATENT DOCUMENTS

| | | | |
|---|---|---|---|
| 6,979,196 B2 | 12/2005 | Nikolskiy et al. | |
| 7,361,020 B2 | 4/2008 | Abolfathi et al. | |

(Continued)

OTHER PUBLICATIONS

Agarwala, et al., "Interactive Digital Photomontage", 2004, ACM SIGGRAPH '04 Conference Proceedings, pp. 1-9.

(Continued)

*Primary Examiner* — Randolph I Chu
(74) *Attorney, Agent, or Firm* — Klein, O'Neill & Singh, LLP

(57) ABSTRACT

Method and system for managing multiple impressions of a patient's jaw for an orthodontic treatment is provided. The method includes scanning at least a first impression and a second impression of same jaw for the orthodontic treatment; determining if the first jaw impression and the second jaw impression have distortion in different areas; selecting the first jaw impression or the second jaw impression as a base impression; and replacing a distorted tooth data from the base impression with data for the same tooth from a non-base impression. The method also includes scanning at least a first jaw impression for the orthodontic treatment; scanning a bite impression for the orthodontic treatment; matching the scanned first jaw impression with the scanned bite impression; comparing bite information with a tooth occlusal surface; and determining if reconstruction is to be performed on the tooth occlusal surface.

11 Claims, 19 Drawing Sheets

(56) References Cited

U.S. PATENT DOCUMENTS

| | | |
|---|---|---|
| 7,730,890 B2 | 6/2010 | Enoch |
| 2002/0048741 A1 | 4/2002 | Jordan et al. |
| 2002/0081554 A1 | 6/2002 | Marshall et al. |
| 2002/0094509 A1 | 7/2002 | Durbin et al. |
| 2002/0187456 A1 | 12/2002 | Craig et al. |
| 2004/0029078 A1 | 2/2004 | Marshall |
| 2004/0191719 A1 | 9/2004 | Kaza |
| 2005/0048432 A1 | 3/2005 | Choi et al. |
| 2005/0106529 A1 | 5/2005 | Abolfathi et al. |
| 2006/0263738 A1 | 11/2006 | Kuo |
| 2007/0025717 A1 | 2/2007 | Raskar et al. |
| 2007/0092850 A1 | 4/2007 | Kaza |
| 2008/0038684 A1 | 2/2008 | Keating et al. |
| 2012/0171642 A1 | 7/2012 | Mehl |

OTHER PUBLICATIONS

Office Action from USPTO dated Apr. 26, 2010 for U.S. Appl. No. 11/678,749.

Office Action from USPTO dated Aug. 4, 2010 for U.S. Appl. No. 11/678,749.

Notice of Allowance from USPTO dated Dec. 23, 2010 for U.S. Appl. No. 11/678,749.

Office Action from USPTO dated Feb. 13, 2014 for U.S. Appl. No. 13/051,759.

Final Office Action from USPTO dated Jul. 30, 2014 for U.S. Appl. No. 13/051,759.

Notice of Allowance from USPTO dated Nov. 21, 2014 for U.S. Appl. No. 13/051,759.

SYSTEM AND METHOD FOR DIGITAL TOOTH IMAGING

CROSS-REFERENCE TO RELATED APPLICATION

This application is a continuation application of application Ser. No. 13/051,759, filed on Mar. 18, 2011; which is a divisional application of application Ser. No. 11/678,749, filed on Feb. 26, 2007, now U.S. Pat. No. 7,916,911, the disclosures of which are incorporated herein by reference in their entireties.

FEDERALLY-SPONSORED RESEARCH OR DEVELOPMENT

Not Applicable

1. FIELD OF THE INVENTION

This invention relates to the field of orthodontics, and more particularly to a system and method for computerized tooth alignment.

2. BACKGROUND OF THE INVENTION

The orthodontics process intends to realign or reposition a patient's teeth to positions where the teeth function optimally and aesthetically. Typically, appliances such as braces are applied to the teeth of the patient by a treating orthodontist. Each appliance exerts continual forces on the teeth which gradually urge the teeth toward their ideal positions. Over a period of time, the orthodontist adjusts the appliances to move the teeth toward their final destination.

The process of attaching the braces to teeth is tedious and painful. Additionally, each visit to the orthodontist is time consuming and expensive. The process is further complicated by uncertainties in determining a final arrangement for each tooth. Generally, the final tooth arrangement is determined by the treating orthodontist who writes a prescription. Traditionally, the prescription is based on the orthodontist's knowledge and expertise in selecting the intended final position of each tooth and without a precise calculation of forces being exerted on the teeth when they contact each other.

Continuous efforts are being made to automate the orthodontics process so that a user can be served better with comparable or better results than traditional techniques.

SUMMARY

In one embodiment, a method for managing plural impressions of a patient's jaw for an orthodontic treatment is provided. The method includes scanning at least a first impression and a second impression of a jaw for the orthodontic treatment; determining if the first jaw impression and the second jaw impression have distortion in different areas; selecting the first jaw impression or the second jaw impression as a base impression; and replacing a distorted tooth data from the base impression with data for the same tooth from a non-base impression.

In another embodiment, system for managing plural impressions of a patient's jaw for orthodontic treatment is provided. The system includes a processing module for determining if a first jaw impression and a second jaw impression have distortion in different areas; selecting the first jaw impression or the second jaw impression as a base impression; and replacing a distorted tooth data from the base impression with data for the distorted tooth from a non-base impression.

In yet another embodiment, a method for reconstructing a tooth occlusal surface for an orthodontic treatment is provided. The method includes scanning at least a first jaw impression for the orthodontic treatment; scanning a bite impression for the orthodontic treatment; matching the scanned first jaw impression with the scanned bite impression; comparing bite information with a tooth occlusal surface; and determining if reconstruction is to be performed on the tooth occlusal surface.

In yet another embodiment, a system for reconstructing a tooth occlusal surface for an orthodontic treatment is provided. The system includes a processing module for matching a scanned first jaw impression with a scanned bite impression; comparing bite information with a tooth occlusal surface; and determining if reconstruction is to be performed on the tooth occlusal surface.

This brief summary has been provided so that the nature of the invention may be understood quickly. A more complete understanding can be obtained by reference to the following detailed description of the preferred embodiments thereof in connection with the attached drawings.

BRIEF DESCRIPTION OF THE DRAWINGS

The foregoing features and other features of the various embodiment will now be described with reference to the drawings of a preferred embodiment. In the drawings, the same components have the same reference numerals. The illustrated embodiment is intended to illustrate, but not to limit the invention. The drawings include the following Figures.

DETAILED DESCRIPTION

In one embodiment, a system and method for automatically aligning teeth is provided. The system can be implemented in software executed by a computing system or by hardware. To facilitate an understanding of the various embodiments, the general architecture and operation of a computing system will be described first. The specific process under the various embodiments is then described with reference to the general architecture.

Figure 1:
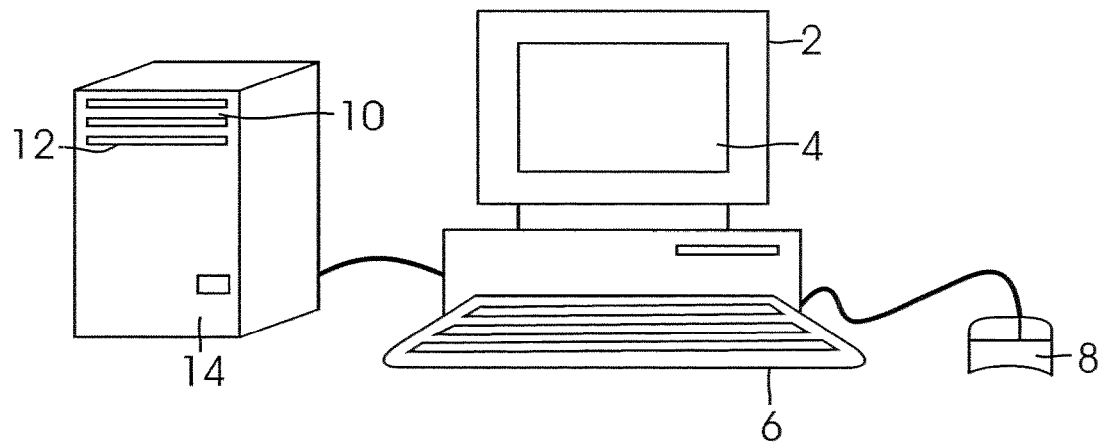
FIG. 1 shows a block diagram of a computing system for executing process steps, according to one embodiment.

Computing System Overview:

FIG. 1 is a block diagram of a computing system for executing computer executable process steps according to one embodiment. FIG. 1 includes a computer (also referred to as host computer) 2 and a monitor 4. Monitor 4 may be a CRT type, a LCD type, or any other type of color or monochrome display. Also provided with computer 2 are a keyboard 6 for entering data and user commands, and a pointing device (for example, a mouse) 8 for processing objects displayed on monitor 4.

Computer 2 includes a computer-readable memory storage device 10 for storing readable data. Besides other programs, storage device 10 can store application programs including computer executable code, according to one embodiment. According to one embodiment, computer 2 can also access computer-readable removable storage devices storing data files, application program files, and computer executable process steps embodying the present invention or the like via a removable memory device 12 (for example, a CD-ROM, CD-R/W, flash memory device, zip drives, floppy drives and others).

A modem, an integrated services digital network (ISDN) connection, or the like also provide computer 2 with a network connection 14, to a network of computers/devices. The network connection 14 allows computer 2 to download data files, application program files and computer-executable process steps embodying the present invention.

It is noteworthy that the adaptive aspects disclosed herein are not limited to the FIG. 1 architecture. For example, notebook or laptop computers, or any other system capable of connecting to a network and running computer-executable process steps, as described below, may be used to implement the various embodiments.

Figure 2:
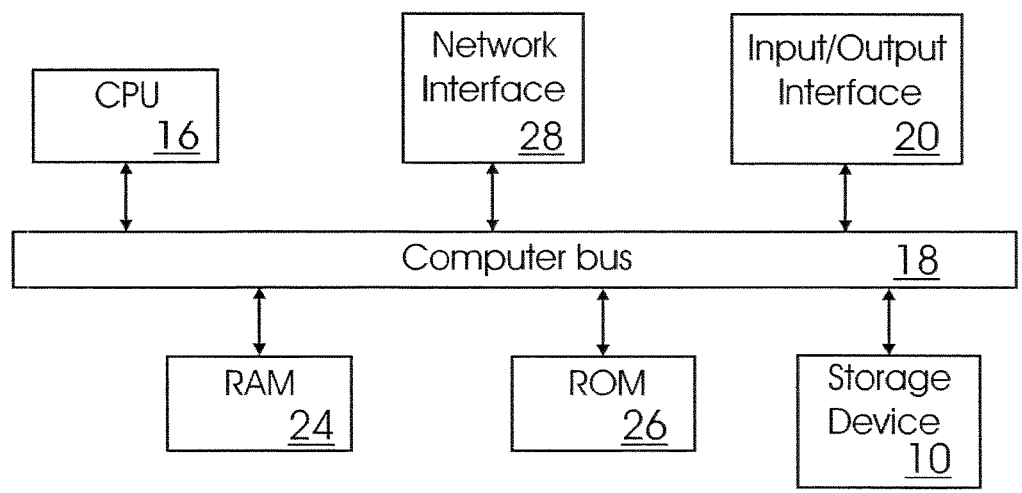
FIG. 2 shows the internal architecture of the computing system of FIG. 1.

FIG. 2 shows a top-level block diagram showing the internal functional architecture of computing system 2 that may be used to execute the computer-executable process steps, according to one embodiment. As shown in FIG. 2, computing system 2 includes a central processing unit (CPU) 16 for executing computer-executable process steps and interfaces with a computer bus 18.

Also shown in FIG. 2 are an input/output interface 20 that operatively connects output display devices such as monitors 4, input devices such as keyboards 6 and a pointing device such as a mouse 8.

Storage device 10 also interfaces to computing system 2 through the computer bus 18. Storage device 10 may be disks, tapes, drums, integrated circuits, or the like, operative to hold data by any means, including magnetically, electrically, optically, and the like. Storage device 10 stores operating system program files, application program files, computer-executable process steps of the present disclosure and other files. Some of these files are stored on storage device 10 using an installation program. For example, CPU 16 executes computer-executable process steps of an installation program so that CPU 16 can properly execute the application program.

Random access memory ("RAM") 24 also interfaces with computer bus 18 to provide CPU 16 with access to memory storage. When executing stored computer-executable process steps from storage device 10, CPU 16 stores and executes the process steps out of RAM 24.

Read only memory ("ROM") 26 is provided to store invariant instruction sequences such as start-up instruction sequences or basic input/output operating system (BIOS) sequences.

Computing system 2 can be connected to other computing systems through a network interface 28 using computer bus 18 and a network connection (for example 14). Network interface 28 may be adapted to one or more of a wide variety of networks, including local area networks, storage area networks, wide area networks, the Internet, and the like.

In one aspect, alignment software may be supplied on a CD-ROM or a floppy disk or alternatively could be read from the network via network interface 28. In yet another aspect, computing system 2 can load alignment software from other computer readable media such as magnetic tape, a ROM, integrated circuit, or a magneto-optical disk. Alternatively, alignment software is installed onto the storage device 10 of computing system 2 using an installation program and is executed using the CPU 16.

In yet another aspect, alignment software may be implemented by using an Application Specific Integrated Circuit that interfaces with computing system 2.

Automated Process Overview:

Methods have been developed to reposition a patient's teeth from an initial tooth arrangement to a final tooth arrangement according to a planned course of treatment using a series of appliances. The process starts when a patient visits an orthodontist/dentist/medical professional/dental laboratory (collectively and interchangeably, as applicable, referred to as the "medical professional"). The medical professional takes jaw impressions that are then sent to an automation center. One such facility is provided by Align Technology Inc., the assignee of the present application.

The automation center digitally scans the jaw impression. The jaw impression is then analyzed by computer modeling software. The modeling software segments all teeth in the jaw impression. Each tooth is stored as an object. Teeth movement is staged over a period of time and appliances are fabricated.

A series of incremental position adjustment appliances are placed over the patient's teeth to gradually reposition the teeth. Each appliance represents a stage in a series of stages for repositioning teeth. The patient wears each appliance until the pressure of each appliance on the teeth can no longer be felt. At that point, the patient replaces the current adjustment appliance with the next adjustment appliance in the series until no more appliances remain.

A problem occurs when a medical professional sends more than one impression for the same jaw. When the same jaw impressions are scanned the distortion between the different jaw impressions can be significant. The adaptive aspects solve this problem, as described below. Prior to describing the actual process, the following overview is provided.

Figure 3:
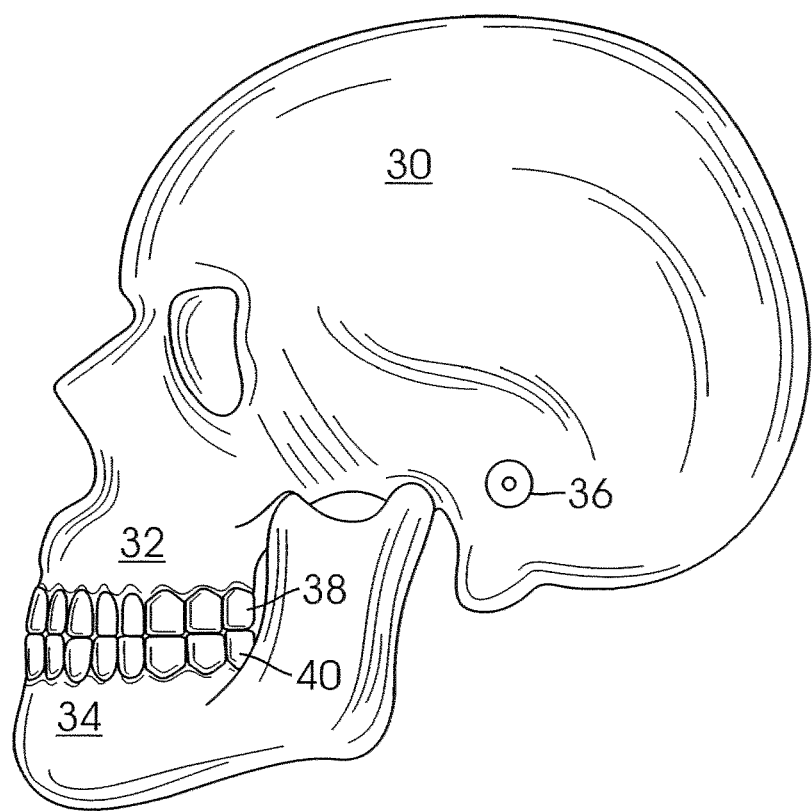
FIG. 3 shows a diagram of the anatomy of a patient's jaw.

FIG. 3 shows a skull 30 with an upper jaw bone 32 and a lower jaw bone 34. The lower jaw bone 34 hinges at a joint 36, which is called a temporal mandibular joint (TMJ). Upper jaw bone 32 is associated with an upper jaw 38, while lower jaw bone 34 is associated with a lower jaw 40.

A computer model of jaws 38 and 40 is generated, and a computer simulation models interactions among the teeth on jaws 38 and 40. The computer simulation allows the system to focus on motions involving contacts between teeth mounted on the jaws and to render realistic jaw movements that are physically correct when jaws 38 and 40 contact each other. The model of the jaw places the individual teeth in a treated position. Further, the model can be used to simulate jaw movements including protrusive motions, lateral motions, and "tooth guided" motions where the path of lower jaw 40 is guided by teeth contacts rather than by anatomical limits of jaws 38 and 40. Motions are applied to one jaw, but may also be applied to both jaws. Based on the occlusion determination, the final position of the teeth can be ascertained.

Figure 4A:
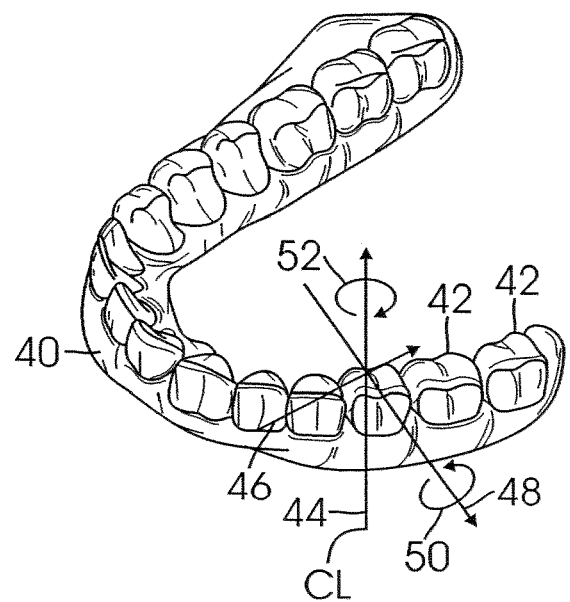
FIG. 4A illustrates in more detail the patient's lower jaw and provides a general indication of how teeth may be moved by the methods and system of the embodiments.

Referring now to FIG. 4A, lower jaw 40 includes a plurality of teeth 42. At least some of these teeth may be moved from an initial tooth arrangement to a desired final tooth arrangement. As a frame of reference describing how a tooth may be moved, an arbitrary centerline (CL) may be drawn through tooth 42. With reference to this centerline (CL), each tooth may be moved in orthogonal directions represented by axes 44, 46, and 48 (where 44 is the centerline). The centerline may be rotated about axis 48 (root angulation) and axis 44 (torque) as indicated by arrows 50 and 52, respectively. Additionally, tooth 42 may be rotated about the centerline, as represented by arrow 52. Thus, all possible free-form motions of the tooth can be performed.

Figure 4B:
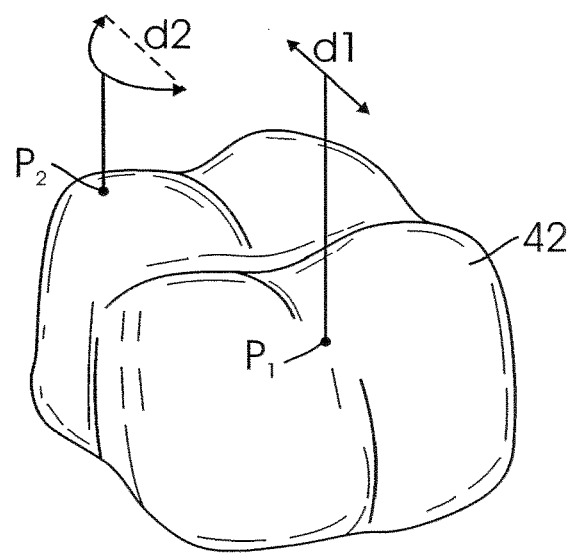
FIG. 4B illustrates a single tooth from FIG. 4A and defines how tooth movement distances are determined.

FIG. 4B shows how the magnitude of any tooth movement may be defined in terms of a maximum linear translation of any point P on tooth 42. Each point P will undergo a cumulative translation as tooth 42 is moved in any of the orthogonal or rotational directions defined in FIG. 4A. That is, while point P will usually follow a nonlinear path, there is a linear distance between any point P in the tooth when determined at any two times during the treatment. Thus, an arbitrary point PI may in fact undergo a true side-to-side translation as indicated by arrow d1, while a second arbitration point P2 may travel along an arcuate path, resulting in a final translation d2. Many aspects of the present disclosure are defined in terms of the maximum permissible movement of point PI induced on any particular tooth. Such maximum tooth movement, in turn, is defined as the maximum linear translation of point PI on the tooth that undergoes the maximum movement for tooth 42 in any treatment step.

Figure 5A:
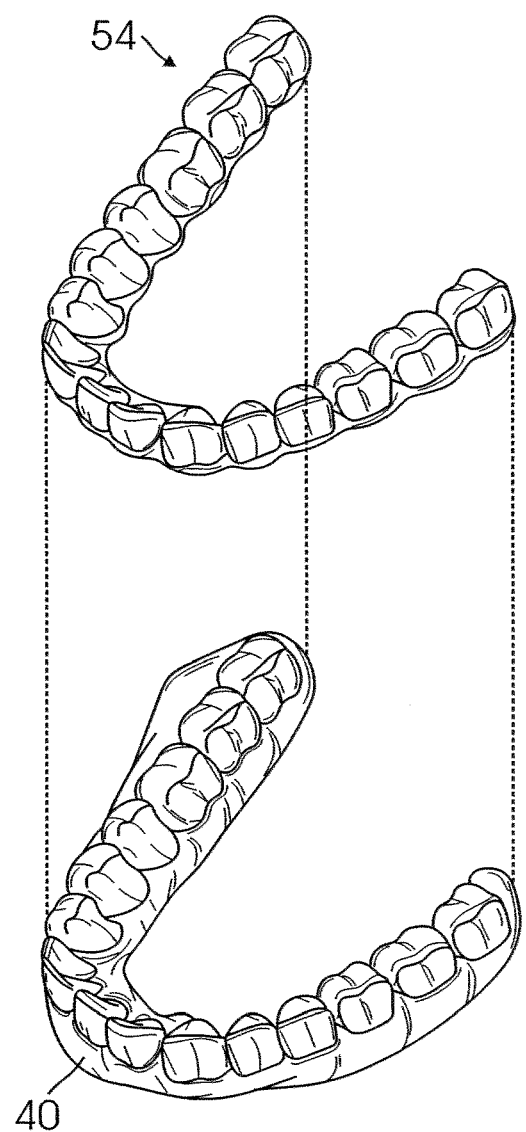
FIG. 5 A shows an example of an appliance used by a patient.
FIG. 5B shows a block diagram of a system for automating tooth alignment, according to one embodiment.

FIG. 5A shows one adjustment appliance 54 which is worn by the patient in order to achieve an incremental repositioning of individual teeth in the jaw as described generally above. Appliance 54 is a polymeric shell having a teeth-receiving cavity. This is described in U.S. Pat. No. 5,975,893 and U.S. Pat. No. 6,450,807, both claiming priority from provisional application Ser. No. 06/050,352, filed Jun. 20, 1997 (collectively the "prior applications"), the full disclosures of which are incorporated by reference in their entirety.

As set forth in the prior applications, each polymeric shell may be configured so that its tooth-receiving cavity has a geometry corresponding to an intermediate or final tooth arrangement intended for appliance 54. The patient's teeth are repositioned from their initial tooth arrangement to a final tooth arrangement by placing a series of incremental position adjustment appliances over the patient's teeth. The adjustment appliances are generated at the beginning of the treatment from an impression taken from the patient's teeth. The patient wears each appliance until the pressure of each appliance on the teeth can no longer be felt. At that point, the patient moves onto the next stage of the planned course of treatment and replaces the current adjustment appliance with the next adjustment appliance in the series until no more appliances remain. Conveniently, the appliances are generally not affixed to the teeth and the patient may place and replace the appliances at any time during the procedure.

The polymeric shell 54 can fit over all teeth present in the upper or lower jaw. Often, only certain one(s) of the teeth will be repositioned while others of the teeth will provide a base or an anchor region for holding appliance 54 in place as appliance 54 applies a resilient repositioning force against the tooth or teeth to be repositioned. In complex cases, however, multiple teeth may be repositioned at some point during the treatment. In such cases, the moved teeth can also serve as a base or anchor region for holding the repositioning appliance.

Polymeric appliance 54 of FIG. 5A may be formed from a thin sheet of a suitable elastomeric polymer, such as Tru-Tain 0.03 in, thermal forming dental material, available from Tru-Tain Plastics, Rochester, Minn. Usually, no wires or other means will be provided for holding the appliance in place over the teeth. In some cases, however, it will be desirable or necessary to provide individual anchors on teeth with corresponding receptacles or apertures in appliance 54 so that the appliance can apply an upward force on the tooth that would not be possible in the absence of such an anchor.

Figure 5B:
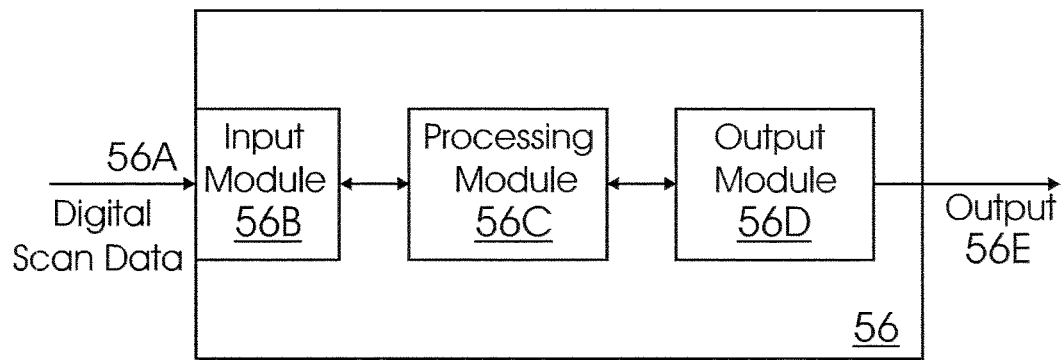

FIG. 5B shows a top-level functional block diagram of a system 56 (alignment software module) that is used for automating the orthodontics process. System 56 has an input module 56B that receives scanned patient impression data. Processing module 56C receives data 56A from input module 56B and a technician/user then segments the individual teeth using digital data 56A. Segmented information is sent to output module 56D that generates output 56E. Output 56E can be stored in a storage device and/or displayed on a display screen.

It is noteworthy that instead of segmentation, surface matching may be used to accomplish the adaptive aspects described below. Commercially available software, such as "Geomagic Qualify" available from Geomagic Inc. may be used to accomplish this task.

It is noteworthy that although FIG. 5B has various components, the present adaptive aspects are not limited to this structure. More or fewer components can be used to implement the functions. Furthermore, different functions can be achieved by software code/hardware or combination of software/hardware.

Figure 6A:
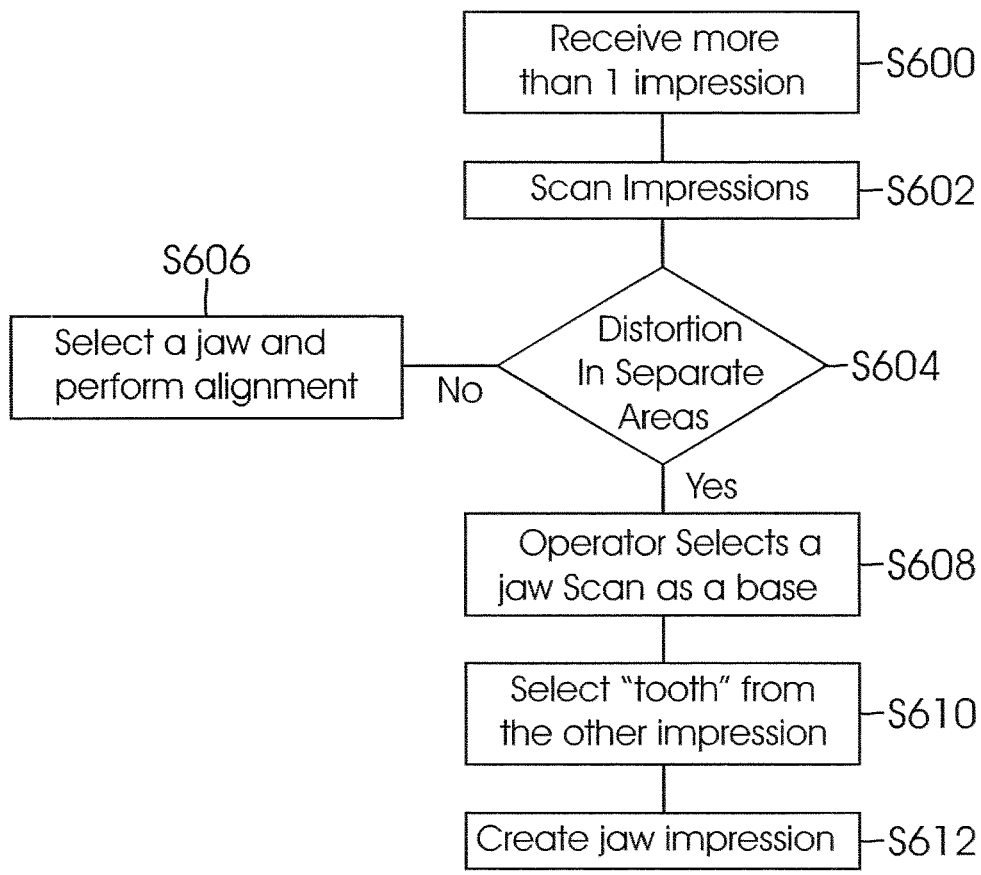
FIG. 6A shows a process flow diagram for handling multiple impressions, according to one embodiment.

Multi-Jaw Impression Alignment Process Flow:

FIG. 6A shows a process flow diagram for managing multiple impressions that are received from a medical professional, according to one embodiment. The process starts in step S600, when the automation center (e.g. Align Technology Inc.) receives more than 1 impression for the same jaw for the same patient. For the sake of convenience and ease of illustration, the discussion below will be based on receiving two impressions for a jaw. It is noteworthy that the adaptive aspects of the present disclosure are not limited to any particular number of impressions. There may be a number of reasons why two impressions of the same jaw may be sent. For example, the medical professional treating the patient may not have been satisfied with the first impression and decided to send another impression.

In step S602, both the impressions are scanned. A digital image is created for both the impressions. A scanning system (not shown) is used to scan the three-dimensional jaw impressions. Thereafter, the scanned imaged is segmented or a surface match using commercial software, for example, Geomagic Qualify is used to duplicate a mesh from one tooth to another.

In step S604, a user using system 56 first aligns both jaw impressions and matches them within certain parameters. For example, parameters include exclusion of certain teeth that may be misaligned, while matching undistorted corresponding teeth between two arches, as discussed below. The user examines both impressions after the alignment and determines if the two impressions have distortion in separate areas/teeth. If the answer is no, then one of the impressions is selected and the process continues (step S606).

Figure 6B:
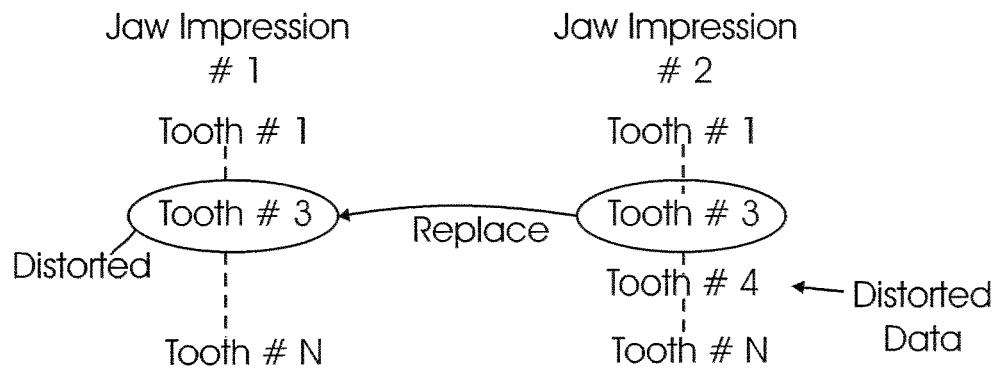
FIG. 6B shows an example of a hierarchical tree where every tooth is an object, according to one embodiment.

If in step S604, the user determines that there is distortion in two separate teeth, then in step S608, one of the jaw impression is selected as a base impression. This is illustrated in FIG. 6B where Tooth #3 for impression number 1 has distortion, while Impression number 2 has distortion in Tooth #4. As an example, Impression #1 is selected as a base for detailing the teeth and for proper alignment. If one impression has less distortion than the second impression, then the impression with less distortion is used as a base.

In step S610, the user having selected a base impression, swaps tooth image/data for the distorted tooth from the non-base impression where the corresponding tooth is undistorted. For example, as shown in FIG. 6B, tooth #3 from jaw impression #1 is swapped with tooth #3 from jaw impression 2. Since each tooth is stored as an individual object, the tooth data (or object) is exchanged efficiently. It is noteworthy that more than one tooth object can be swapped between the impressions. Also, instead of swapping the tooth, the user can use tooth #3 from impression #2 as a template to fix the distortion in tooth #3 for impression #1.

In step S612, the jaw impression is completed.

Figure 6C:
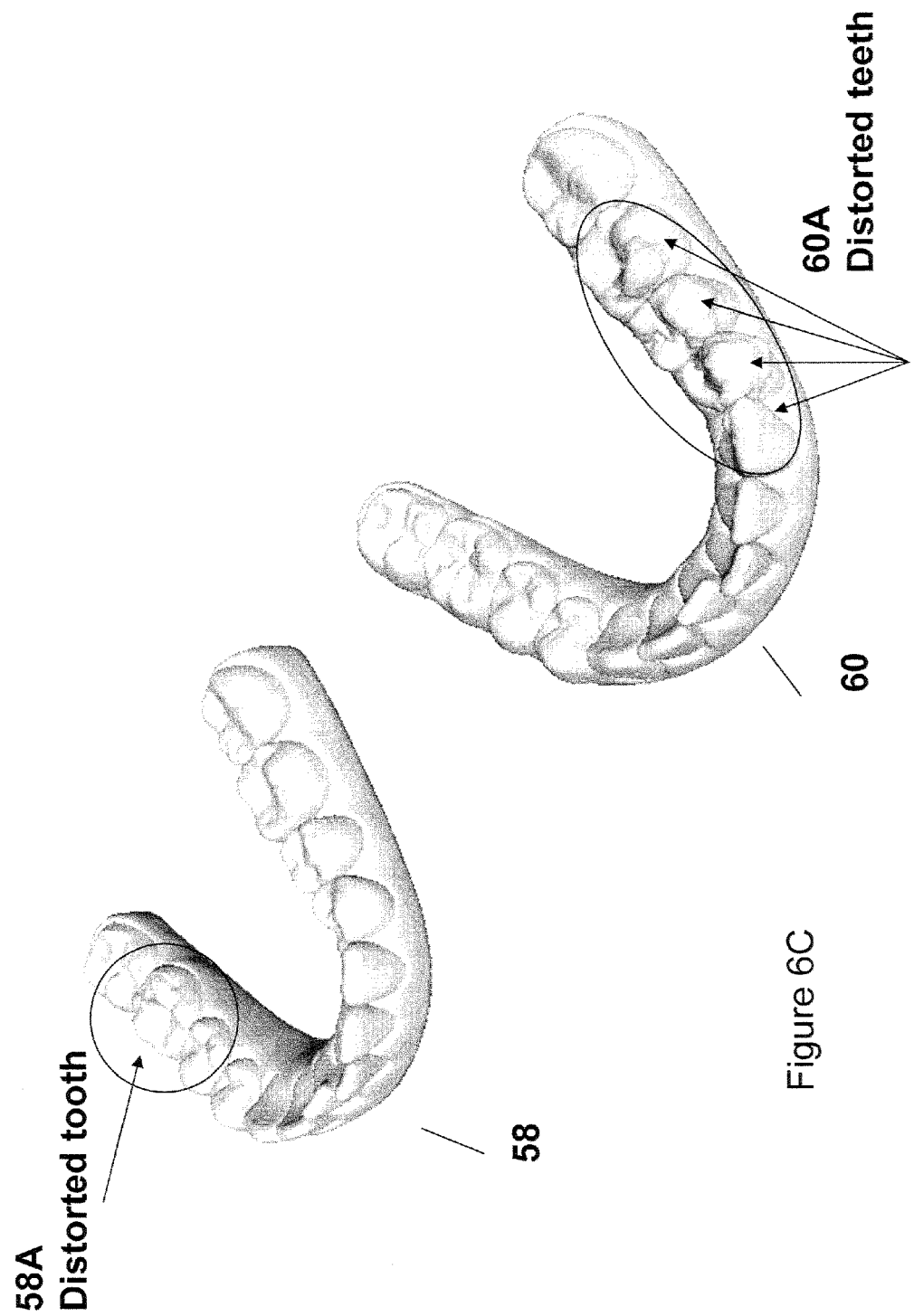
FIGS. 6C-6F show examples for handling multiple impressions, according to one embodiment.
Figure 6D:
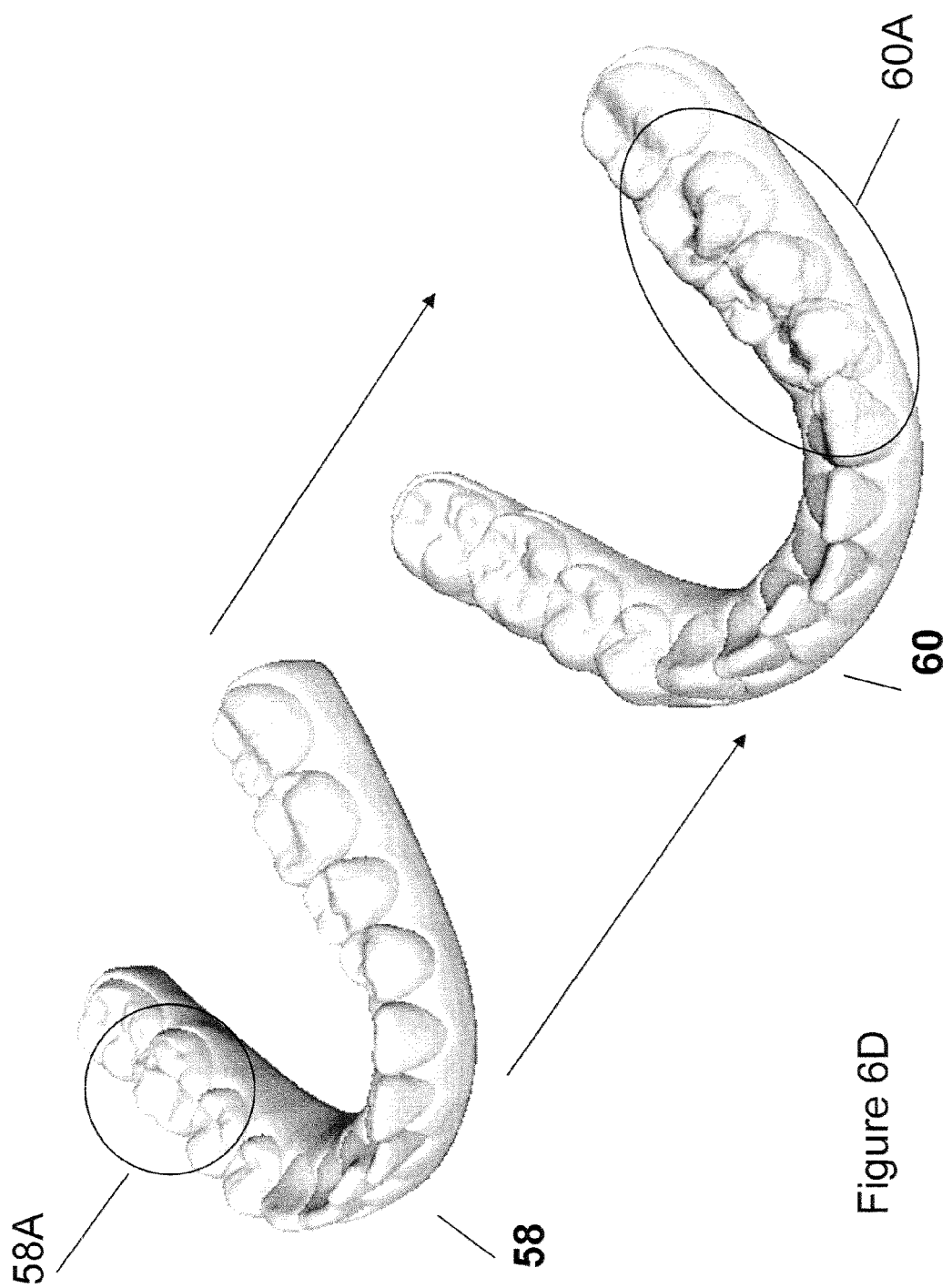
Figure 6E:
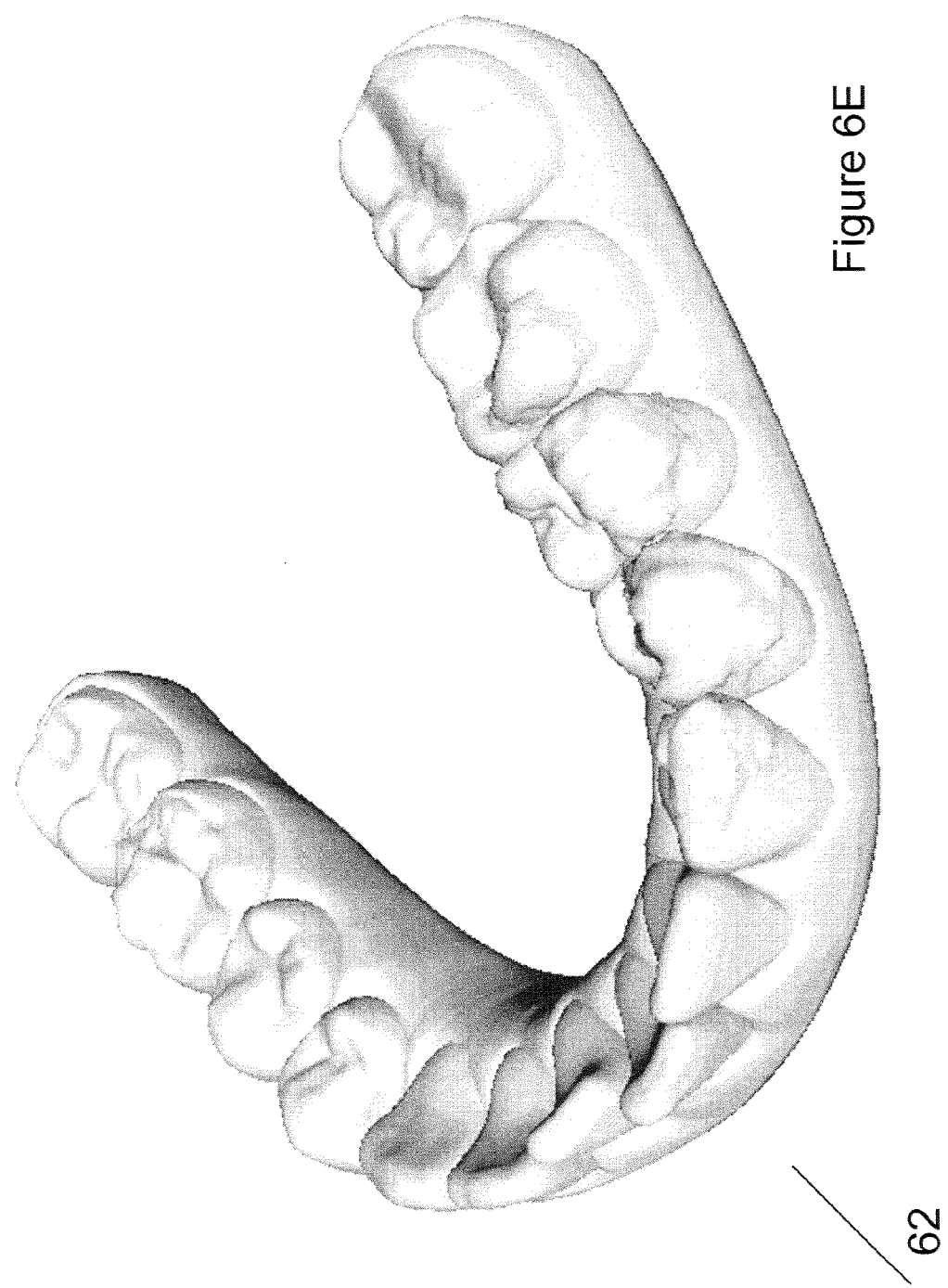
Figure 6F:
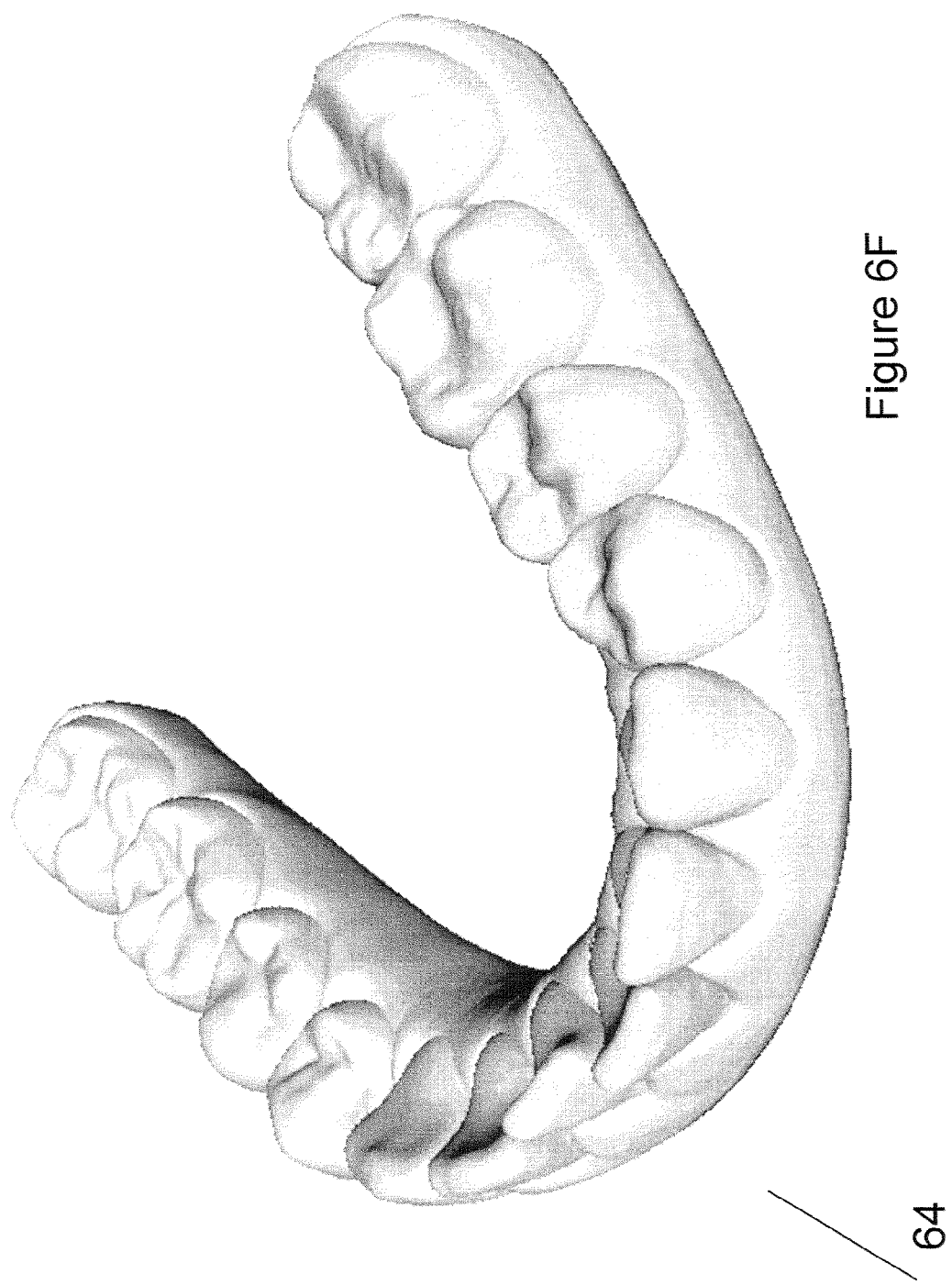

FIGS. 6C-6F show screen shots from a computer model for executing the process steps of FIG. 6A. FIG. 6C shows two impressions 58 and 60 that have distortion in different areas, 58A and 60A, respectively. FIG. 6D shows impression 58 as being superimposed on impression 60. Undistorted teeth are kept and distorted teeth are excluded in the alignment process. FIG. 6E shows the superimposed results (62). Both arches for impressions 58 and 60 are overlaid into the same virtual position. FIG. 6F shows the final combined impressions (64) blended into one for treatment. The distorted regions 58A and 60A are eliminated and replaced by anatomically proper teeth.

One advantage of the foregoing process is that the medical professional does not have to take another impression. A technician can also pick and match data from more than one source to create a complete digital object. This is helpful to the medical professional and to the patients.

Figure 7A:
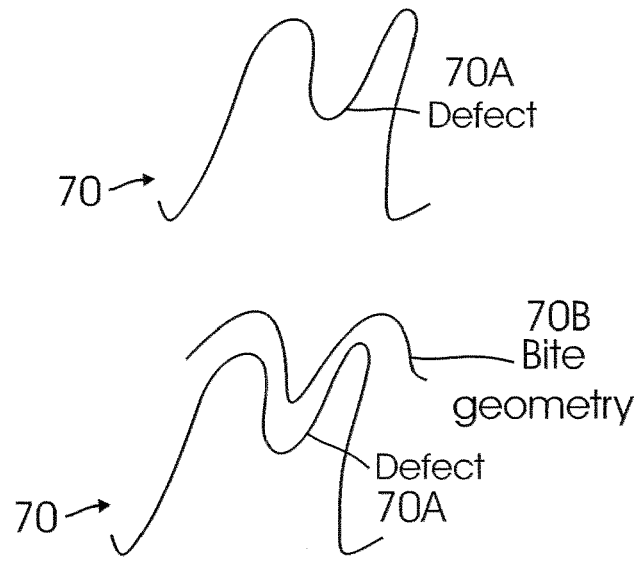
FIG. 7A shows an example of a bite scan, used according to one embodiment.
Figure 7B:
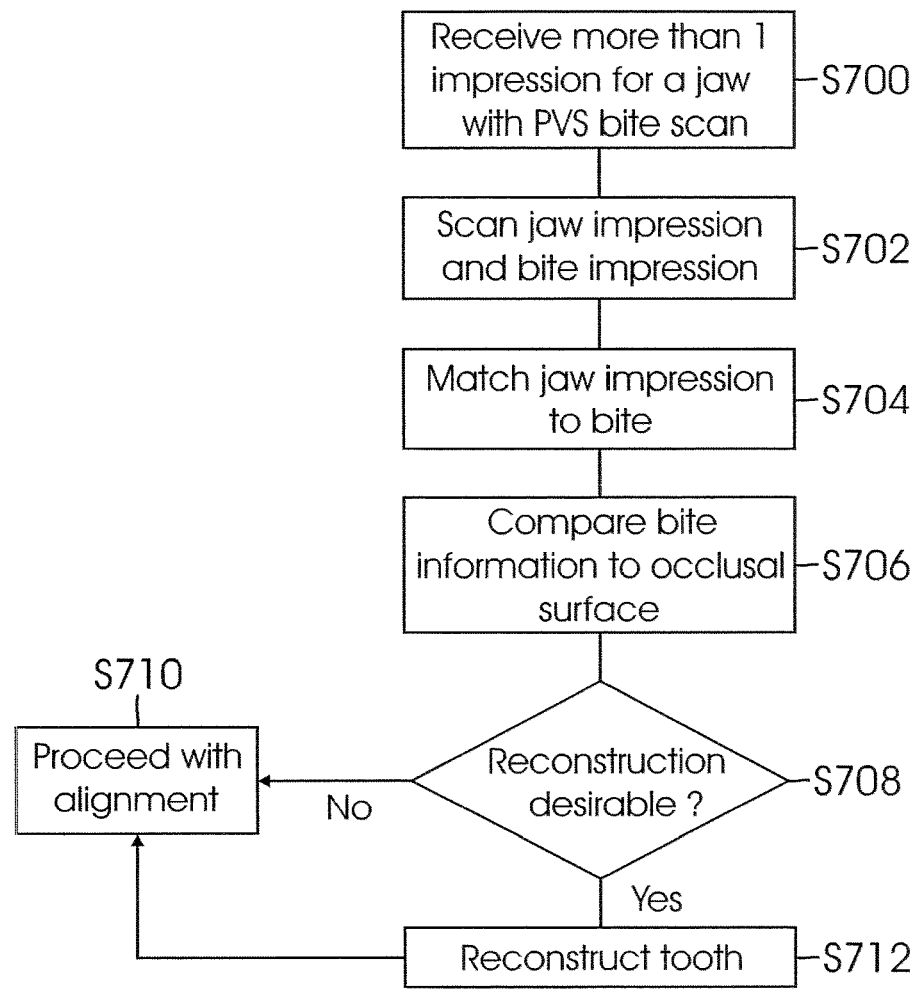
FIG. 7B shows a flow chart for using bite scan information, according to one embodiment.

Multiple Impression/Bite Data:

In some instances, a dental laboratory may provide more than one impression and also provide a bite scan for the jaws. The bite scan is used to fill in defects that occur in a jaw impression. FIG. 7A shows an example of a tooth impression 70 with a defect 70A. Bite scan geometry 70B is used to fill in the defect 70A. FIG. 7B shows a process flow diagram, similar to the process flow diagram of FIG. 6A, except in this case, bite scan information is used to detail a tooth. The term detail as used herein means filling in defects in a tooth scanned image.

Turning in detail to FIG. 7B, in step S700, an automation center receives more than 1 impression, each with a PVS bite impression. PVS bite impressions are provided by dental laboratories. Typically, a laboratory will provide the bite impression if there is a defect in a jaw impression. As discussed above, the bite impression is used to detail the teeth.

In step S702, the bite impression and the jaw impressions are digitally scanned. In step S704, the jaw impressions are digitally matched to the bite impression. In step S706, the process compares bite information with a tooth occlusal surface. If reconstruction is needed (step S708), then the tooth is reconstructed in step S712. In this step, processing module 56C reconstructs missing data, removes excess data or fixes distortion. If reconstruction is not needed, then the process moves to alignment in step S710, which is similar to the steps shown in FIG. 6A.

Figure 7C:
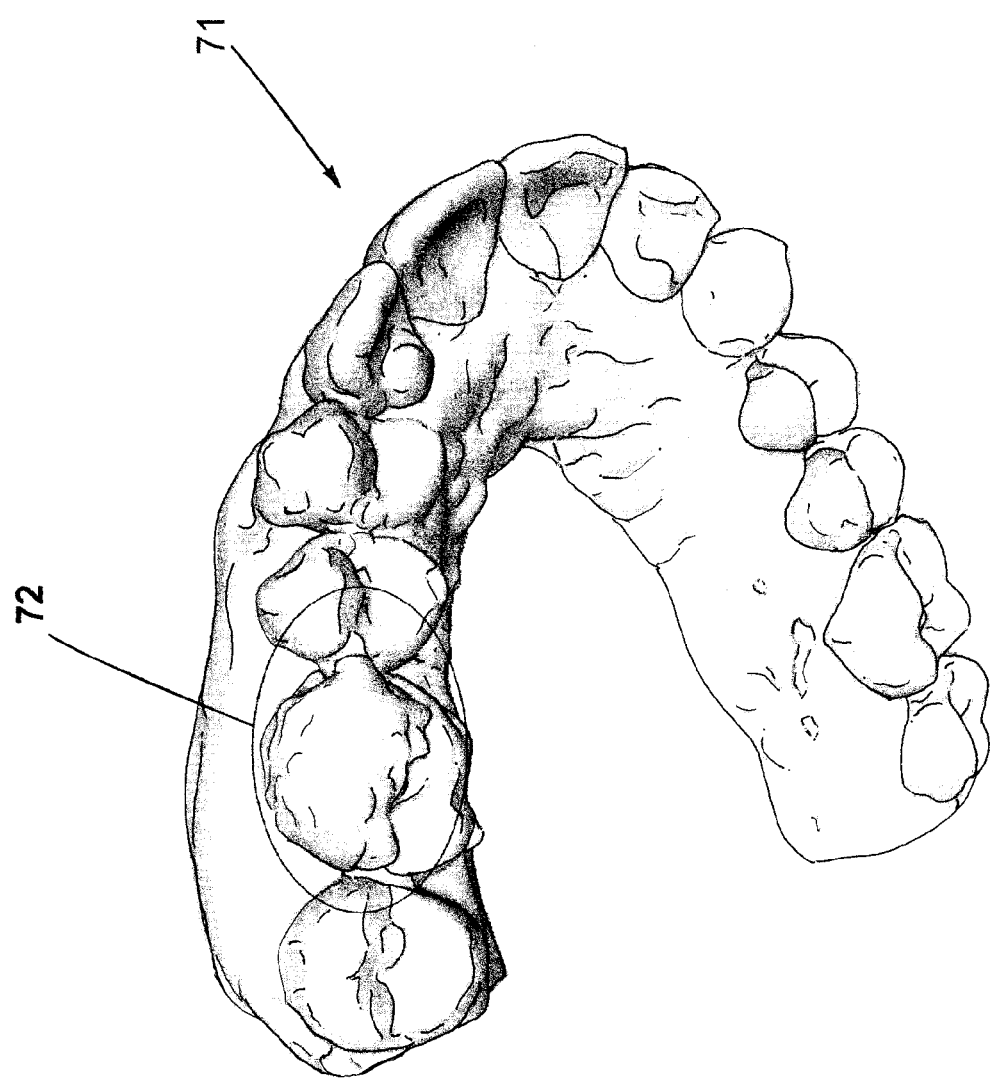
FIGS. 7C-7J show examples of using bite scan, according to one embodiment.
Figure 7D:
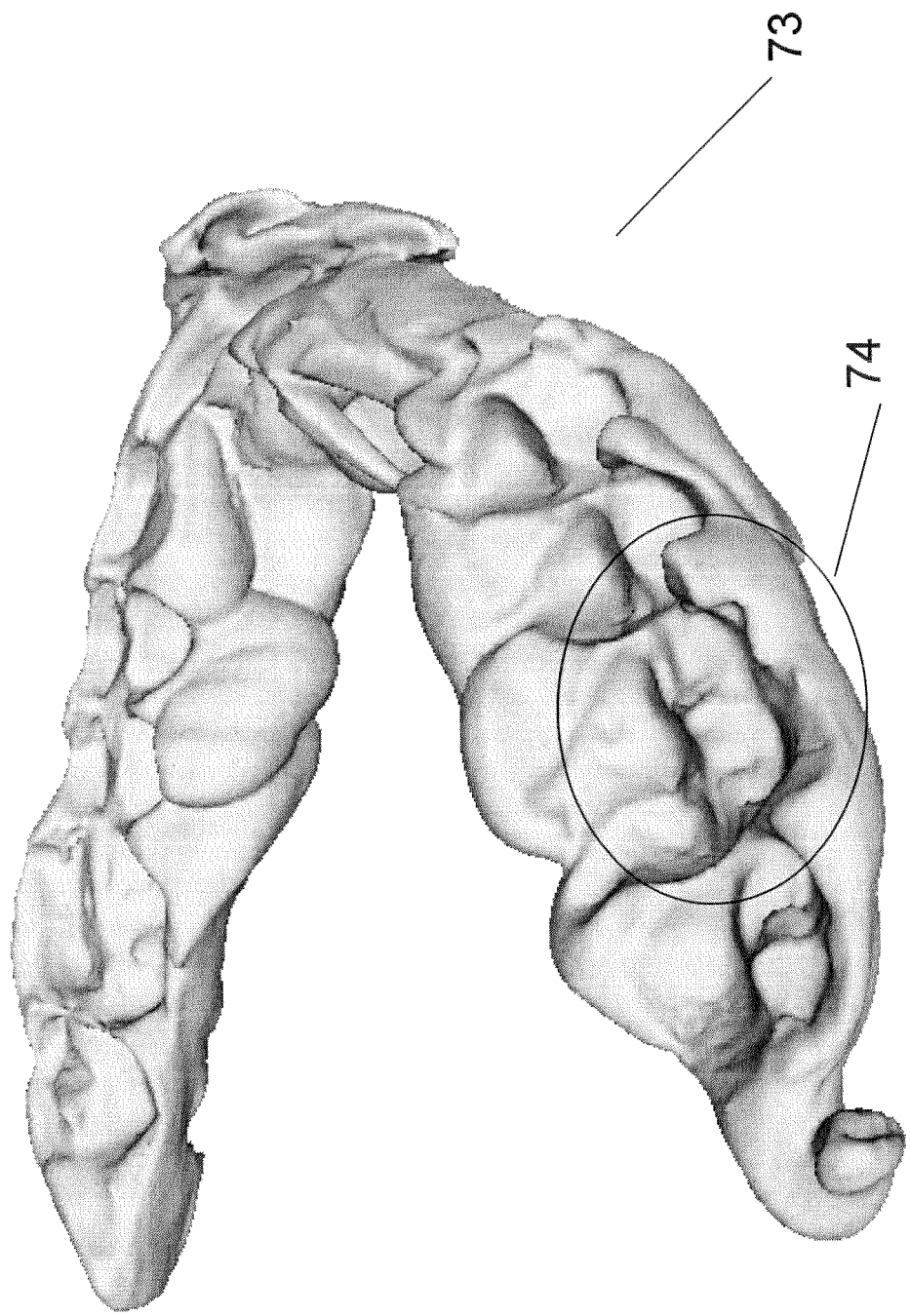

FIGS. 7C-7J show screen shots illustrating the process steps of FIG. 7B. FIG. 7C shows a scanned digital jaw impression 71 with distortion in tooth (or region) 72. This is based on the impression that is received from the medical professional. FIG. 7D shows a scanned model 73 showing bite registration between plural teeth. This is based on information and model/bite data provided by a medical professional. The tooth that needs to be detailed is shown as 74. From an image processing perspective, 73 is a negative for an image 71.

Figure 7E:
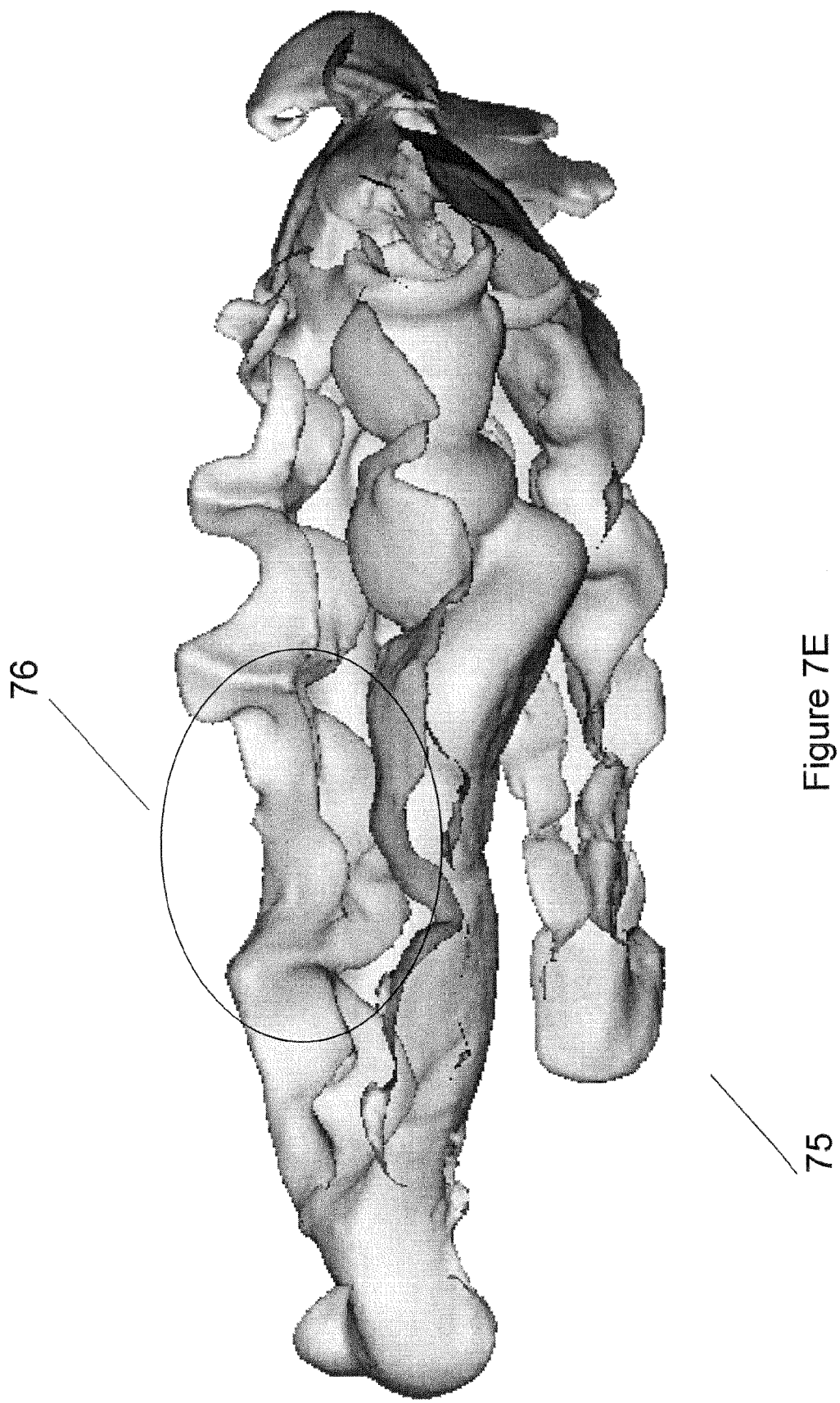
Figure 7:
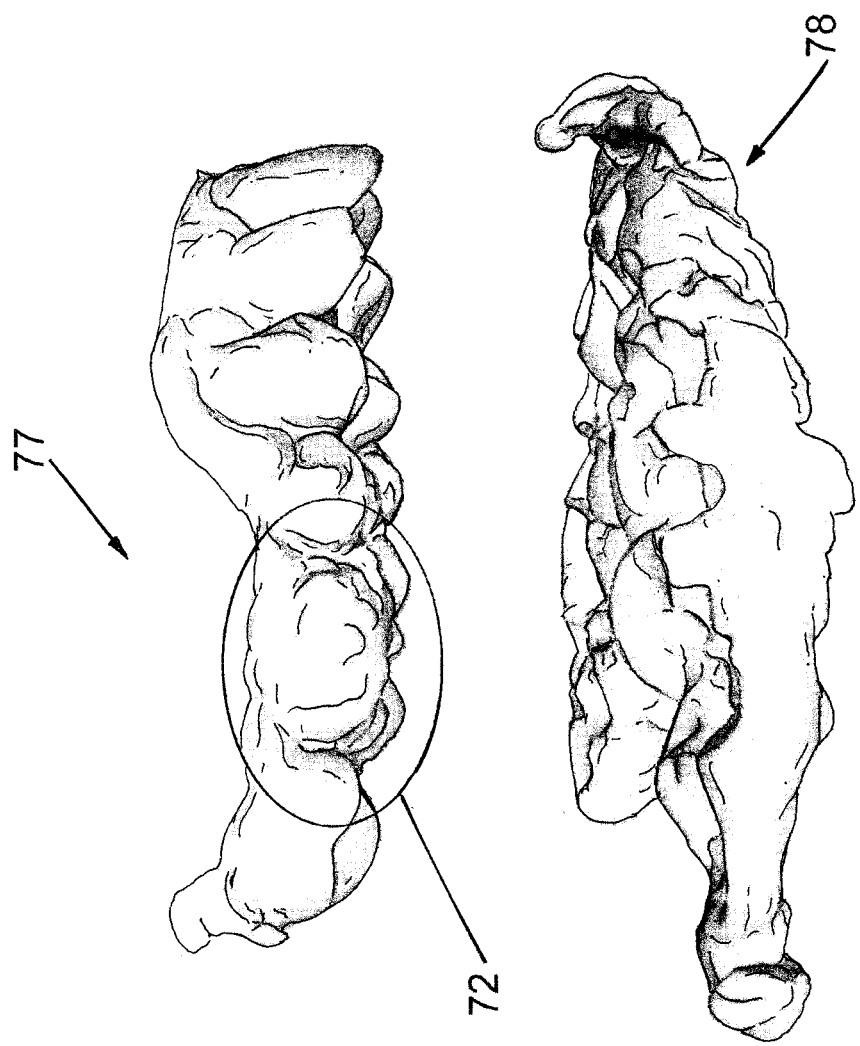

FIG. 7E shows proper tooth anatomy (76) in PVS bite registration 75. A user can see this by simply toggling through the image (75). FIG. 7F shows a distorted PVS impression or model 77 based on a model received from the medical professional. This shows the distorted tooth 72 (FIG. 7C). FIG. 7F shows PVS bite registration 78 for both sides of a mouth. This again is based on bite information received from a medical professional.

Figure 7G:
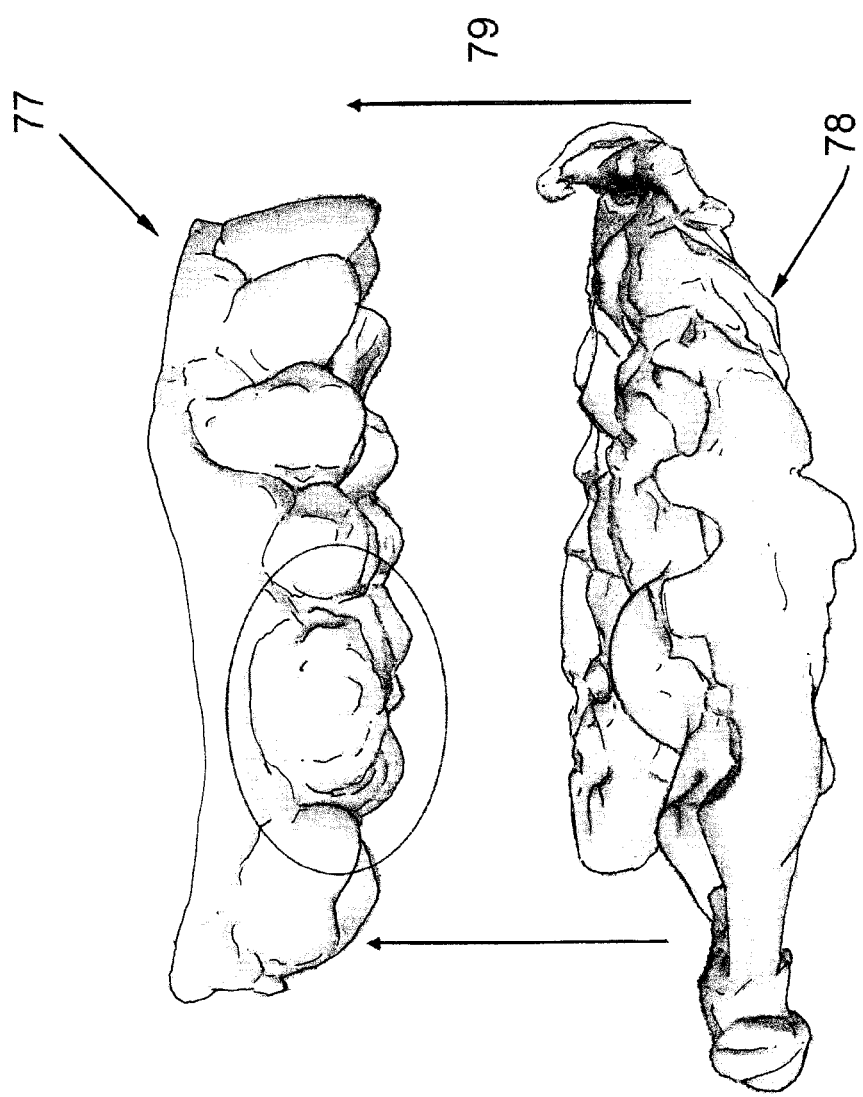
Figure 7H:

FIG. 7G shows bite registration 78 as being overlaid (79) on distorted PVS impression/model 77. FIG. 7H shows the virtual overlay 80 of PVS bite registration 78 and impression 77. In one aspect, tooth crown anatomy is used as a guide for positioning PVS bite registration into proper coordinates.

Figure 7I:
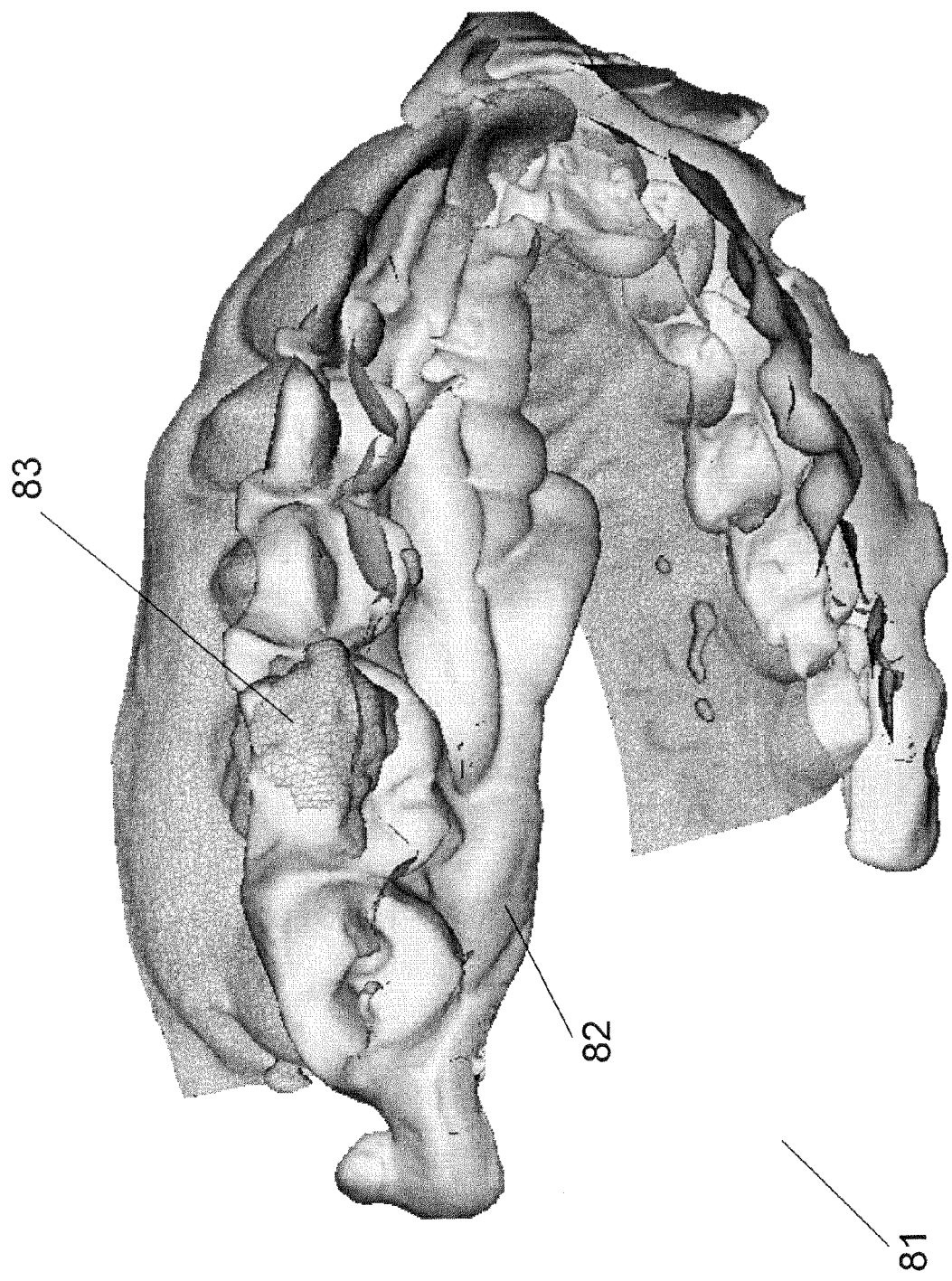
Figure 7J:
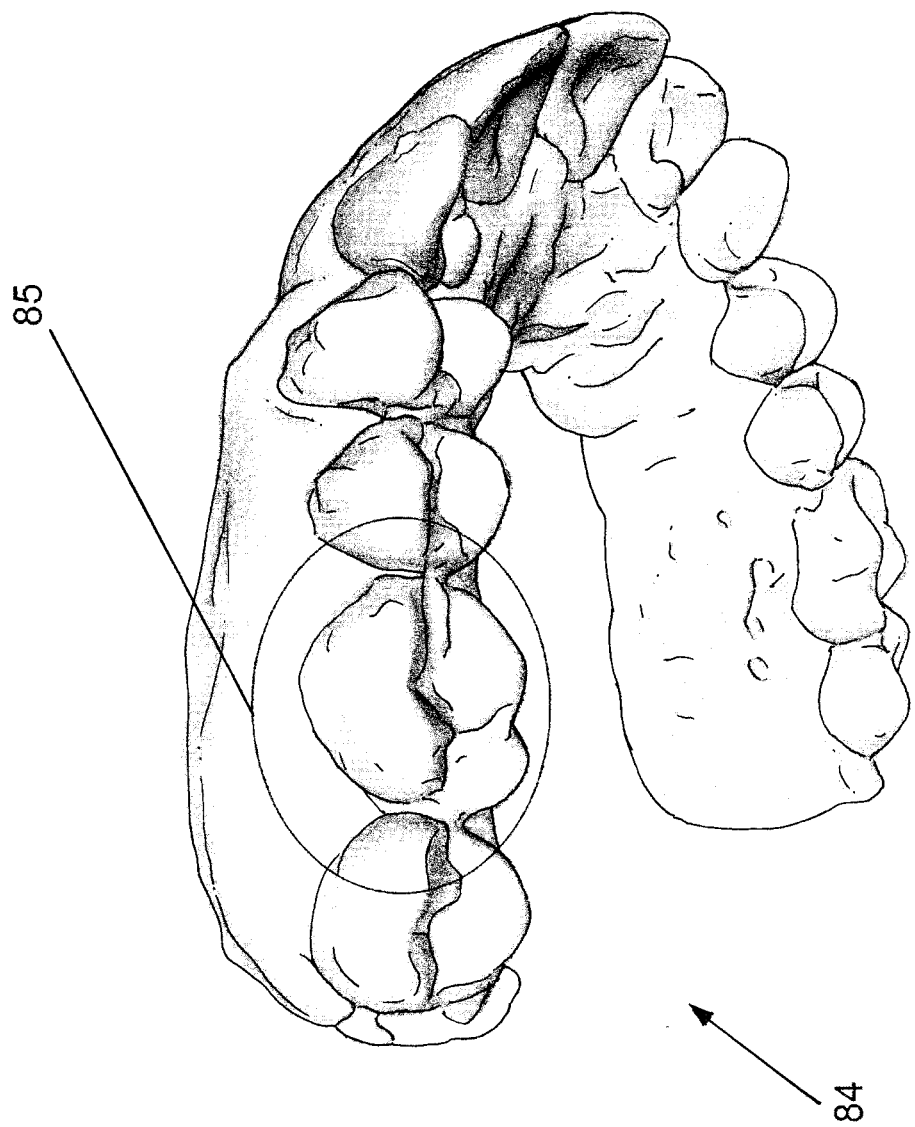

FIG. 7I shows a modeled shot 81 with a meshed area 83 and PVS area 82. The meshed area is used to remove the distortion (72, FIG. 7C) and rebuild the tooth structure. FIG. 7J shows a rebuilt model 84. The rebuilt area is shown as 85.

In one aspect of the present disclosure, digital tooth detailing is automated. This also allows for automatic bite creation for complex cases. Furthermore, missing or distorted information is identified on the occlusal surface and is also corrected automatically.

It is noteworthy that the foregoing embodiments are not limited to any particular number of jaw impressions, i.e. more than two impressions may be used the same result. Furthermore, more than two impressions with a PVS bite scan may also be used to for defect correction.

While the present disclosure is described above with respect to what is currently considered its preferred embodiments, it is to be understood that the disclosure is not limited to that described above. To the contrary, the disclosure is intended to cover various modifications and equivalent arrangements within the spirit and scope of the appended claims.

What is claimed is:

1. A method for building a digital model of a patient's jaw with a reconstructed tooth occlusal surface image, comprising:
    (a) creating a digitized jaw image from a scan of at least a portion of the patient's jaw, the digitized jaw image including a first digitized image of the tooth occlusal surface;
    (b) creating a digitized bite image from a scan of at least a portion of the patient's jaw in a bite configuration, the digitized bite image including a second digitized image of the tooth occlusal surface;
    (c) matching the digitized jaw image with the digitized bite image;
    (d) comparing the first and second digitized images of the tooth occlusal surface; and
    (e) if the comparison of the first and second digitized images of the tooth occlusal surface indicates at least one of missing image data and distortion in the first digitized image of the tooth occlusal surface, digitally correcting the first digitized image of the tooth occlusal surface by reconstructing any missing image data and reducing any distortion in the first digitized image of the tooth occlusal surface using image data from the second digitized image of the tooth occlusal surface.

2. The method of claim 1, wherein the matching step comprises virtually overlaying the digitized bite image on the digitized jaw image.

3. The method of claim 1, further comprising:
(f) building a digital model of the patient's jaw using the corrected first d gitized image of the tooth occlusal surface.

4. The method of claim 1, further comprising:
(f) using the bite image to determine if occlusal reconstruction is to be performed on the tooth occlusal surface.

5. The method of claim 1, wherein the step of digitally correcting the first digitized image of the tooth occlusal surface includes digitally reshaping the first digitized image of the tooth occlusal surface.

6. A system for building a digital model of a patient's jaw with a reconstructed image of a tooth occlusal surface, comprising:
a processor-executable processing module configured for (a) matching (i) a digitized jaw image including a first digitized image of the tooth occlusal surface, with (ii) a digitized bite image including a second digitized image of the tooth occlusal surface; (b) comparing the first and second digitized images of the tooth occlusal surface; (c) determining if the comparison of the first and second digitized images of the tooth occlusal surface indicates at least one of missing image data and distortion in the first digitized image of the tooth occlusal surface; and (d) if the comparison indicates any missing image data or any distortion in the first digitized image of the tooth occlusal surface, digitally correcting the first digitized image of the tooth occlusal surface by reconstructing any missing image data and reducing any distortion in the first digitized image of the tooth occlusal surface using image data from the second digitized image of the tooth occlusal surface.

7. The system of claim 6, further comprising a digitizing module configured for creating the digitized jaw image from a scan of at least a portion of the patient's jaw, and for creating the digitized bite image from a scan of the patient's jaw in a bite configuration.

8. The system of claim 6, wherein the processor-executable processing module is further configured for (e) building a digital model of the patient's jaw using the corrected first digitized image of the tooth occlusal surface.

9. The system of claim 6, wherein the processor-executable processing module is configured to compare the first and second digitized images of the tooth occlusal surface by virtually overlaying the digitized bite image on the digitized jaw image.

10. The system of claim 6, wherein processor-executable processing module is configured to use the bite image to determine if occlusal reconstruction is to be performed on the tooth occlusal surface.

11. The system of claim 6, wherein the processor-executable processing module missing data is configured to digitally correct the first digitized tooth occlusal surface image by digitally reshaping the first digitized image of the tooth occlusal surface.

* * * * *

UNITED STATES PATENT AND TRADEMARK OFFICE
CERTIFICATE OF CORRECTION

PATENT NO.        : 9,301,814 B2
APPLICATION NO.   : 14/670137
DATED             : April 5, 2016
INVENTOR(S)       : Kaza et al.

Page 1 of 1

It is certified that error appears in the above-identified patent and that said Letters Patent is hereby corrected as shown below:

In the claims,
In column 9, line 3, in Claim 3, delete "d gitized" and insert -- digitized --, therefor.

Signed and Sealed this
Twenty-eighth Day of June, 2016

Michelle K. Lee
*Director of the United States Patent and Trademark Office*